United States Patent [19]

Knifton

[11] Patent Number: 5,157,161
[45] Date of Patent: Oct. 20, 1992

[54] ONE-STEP SYNTHESIS OF METHYL T-BUTYL ETHER FROM T-BUTANOL USING HYDROGEN FLUORIDE-MODIFIED MONTMORILLONITE CLAYS

[75] Inventor: John F. Knifton, Austin, Tex.

[73] Assignee: Texaco Chemical Company, White Plains, N.Y.

[21] Appl. No.: 803,834

[22] Filed: Dec. 9, 1991

[51] Int. Cl.$^5$ .............................................. C07C 41/09
[52] U.S. Cl. .................................................... 568/698
[58] Field of Search ........................................ 568/698

[56] References Cited

U.S. PATENT DOCUMENTS 5,099,072  3/1942  Knifton .............................. 568/698

Primary Examiner—Howard T. Mars
Attorney, Agent, or Firm—Jack H. Park; Kenneth R. Priem; Cynthia L. Kendrick

[57] ABSTRACT

A method is disclosed wherein t-butanol is reacted with methanol in a reaction zone in the presence of a catalyst to provide methyl-tert-butyl ether and the improvement of accomplishing the reaction in one-step which comprises:

a. contacting the reactants with a montmorillonite silica-alumina catalyst which has been treated with hydrogen fluoride;

b. continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain the methyl tert-butyl product, wherein under certain conditions the product mix separates into an isobutylene-MTBE product-rich phase and a heavier aqueous methanol phase.

14 Claims, 1 Drawing Sheet

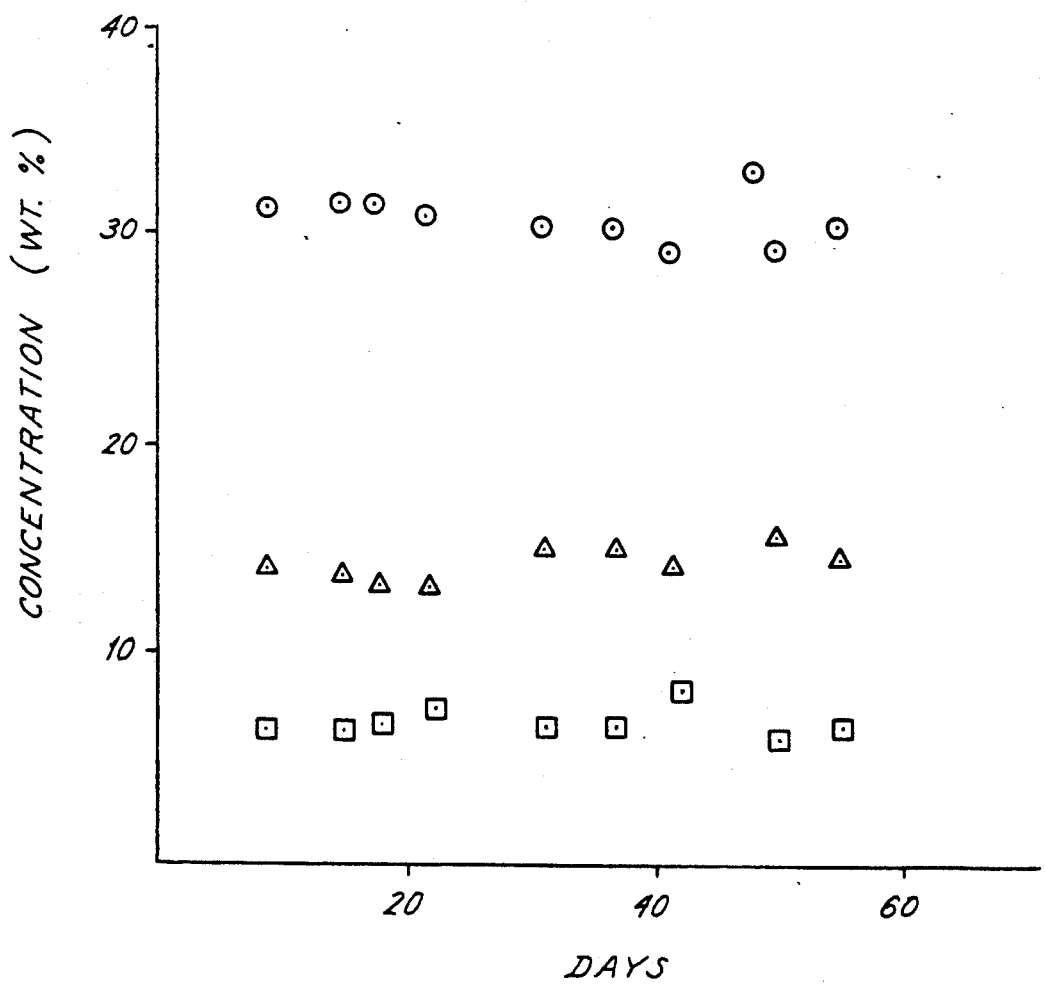

ONE-STEP SYNTHESIS OF METHYL T-BUTYL ETHER FROM T-BUTANOL USING HYDROGEN FLUORIDE-MODIFIED MONTMORILLONITE CLAYS

CROSS-REFERENCE

This application is related to U.S. Pat. Nos. 4,827,048 and 4,822,921 and to application Ser. Nos. 07/494,280 now U.S. Pat. Ser. No. 5,099,072, 07/724,071 and 07/494,281 and to Ser. Nos. 07/677,192 now U.S. Pat. Ser. No. 5,059,725 and 07/663,527 now U.S. Pat. Ser. No. 5,081,318.

It is also related to copending U.S. Ser. Nos. 07/724,071; 07/745,177 and 07/783,015.

FIELD OF THE INVENTION

This invention concerns an improved process for preparing methyl tertiary butyl ether by the reaction of tertiary butanol (TBA) and methanol (MeOH) in the presence of a catalyst comprising a hydrogen fluoride-modified clay mineral catalyst containing alumina and silica, such as smectite clays, including montmorillonite silica-alumina clays. The invention is particularly advantageous in that the reaction takes place in one-step, typically MTBE is generated continuously in 30+% concentration in the crude product effluent and product phase separation is in evidence at operating temperatures of 160° C. or greater, with the crude product mix separating into an isobutylene-MTBE product-rich phase and a heavier aqueous methanol phase.

BACKGROUND OF THE INVENTION

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether (MTBE) are based upon the liquid-phase reaction of isobutylene and methanol (Eq. 1), catalyzed by a cationic ion-exchange resin (see, for example: Hydrocarbon Processing, Oct. 1984, p. 63; Oil and Gas J., Jan. 1, 1979, p. 76; Chem. Economics Handbook-SRI, Sept. 1986, p. 543–7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

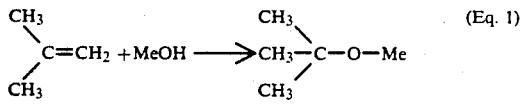

(Eq. 1)

With the expanding use of MTBE as an acceptable gasoline additive, however, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since t-butanol (TBA) is readily available commercially through isobutane oxidation.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate plus ether-methanol bottoms, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In an article titled "Catalysis: Selective Developments", Chem. Systems Report 84-3, 239–249, at section 3.4320, the unusual properties of smectite clays which make them of interest as catalysts are discussed. These compositions are layered and exhibit a 2:1 relationship between tetrahedral and octahedral sites. In addition the combination of cation exchange, intercalation and the fact that the distance between the layers can be adjusted provide interesting possibilities.

There is a discussion of clay mineral catalysts, including "acid" montmorillonite clay catalysts in "Progress in Inorganic Chemistry", Vol. 35, p. 41 (1987). The process of pillaring this type of catalyst is discussed. Pillaring can convert a clay lamellar solid into a more heat resistant two dimensional zeolite material.

G.B. Pat. No. 2,179,563 (1987) discloses the use of modified layered clay catalysts in reactions capable of catalysis by protons. Of particular interest in this invention were the three-layer sheet types, such as smectites, micas and vermiculites composed of successive layers of tetrahedral silica, octahedral alumina and tetrahedral silica which can exhibit swelling properties.

U.S. Pat. No. 4,590,294 discloses a process for the production of an ester comprising reacting an olefin from the group consisting of ethylene, hex-1-ene, hept-1-ene, oct-1-ene, 4-methylpent-1-ene, hex-2-ene, 1,5-hexadiene and cyclohexene with a carboxylic acid using as a catalyst component a hydrogen ion-exchanged layered clay. This reference would not seem to suggest a method for simultaneous dehydration of tert-butanol to iso-butylene and the reaction with methanol to produce MTBE.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungstophosphoric acid or 12-molybdophosphoric acid on an inert support, such as titania.

Copending U.S. patent application Ser. No. 07/494,280 discloses the reaction of butanol and methanol in the presence of acidic montmorillonite clay catalysts having certain identifiable physical parameters.

Copending U.S. patent application Ser. No. 07/677,192 discloses a super acid, sulfuric acid-on-Group IV oxide for preparing MTBE from t-butanol and methanol in one step. In copending U.S. patent application Ser. No. 07/663,527, a Y-type zeolite modified with fluorosulfonic acid is disclosed.

In copending U.S. patent application Ser. No. 07/724,071, there is disclosed a method for one-step synthesis of MTBE from t-butanol using fluorocarbon sulfonic acid polymers on inert supports.

It would be a substantial advance in the art if methyl tertiary butyl ether could be selectively synthesized from tertiary butyl alcohol and methanol in one step using a clay mineral catalyst which allows for rapid conversion of t-butanol.

It has now been discovered that hydrogen fluoride-modified montmorillonite clays can be used as catalysts for the selective synthesis of tertiary butyl alcohol and methanol. The accompanying examples demonstrate good yields of MTBE when using the modified montmorillonite clays of the instant invention, with significantly higher MTBE/isobutylene yields using crude methanol/t-butanol feedstocks over extended periods than with other catalysts.

SUMMARY OF THE INVENTION

In accordance with certain of its aspects, the novel method of this invention for preparing methyl tert-butyl ether from tertiary butyl alcohol (t-butanol) and methanol in one-step comprises reacting tertiary butyl alcohol and methanol in the presence of a catalyst comprising hydrogen fluoride-modified montmorillonite silica-alumina clays at elevated temperature and moderate pressure. Examples demonstrate the particular effectiveness of a hydrogen fluoride-modified Engelhard Grade F2C montmorillonite clay.

BRIEF DESCRIPTION OF THE DRAWINGS

FIG. 1 illustrates the performance of the catalyst of Example 3 over a 50 day period in terms of wt % concentration of MTBE, isobutylene and t-butanol in the product.

DESCRIPTION OF THE INVENTION

Preparation of the product of this invention may be carried out typically by reacting tertiary butyl alcohol and methanol in the presence of an etherification catalyst. The etherification is carried out in one step and the catalyst preferably comprises a montmorillonite silica-alumina clay catalyst modified with hydrogen fluoride.

The reaction can be represented by the following:

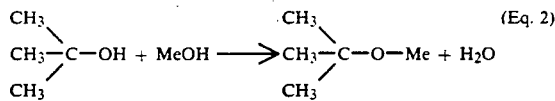

Generally the methanol and t-butanol coreactants may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of methanol in the liquid feed is desirable. The most preferred methanol-to-tertiary butanol molar ratio is from 1:1 to 5:1.

The synthesis of Eq. 2 can also be conducted where the t-butanol and methanol reactants are mixed with certain other components including water, ketones such as acetone ($Ac_2O$), peroxides and hydroperoxides such as di-t-butyl peroxide (DTBP) and allyl t-butyl peroxide, as well as esters such as t-butyl formate (TBF). Typically each of said classes of components makes up less than 10% of the total feed mixture.

The same process may also be applied to the preparation of other alkyl tertiary alkyl ethers. For example, said process may be applied to the reaction of a $C_1$-$C_6$ primary alcohol such as methanol, ethanol, n-propanol and n-hexanol with a $C_4$-$C_{10}$ tertiary alcohol such as, for example, tertiary butanol and tertiary amyl alcohol. Reaction of methanol with tertiary amyl alcohol (2-methyl-2-butanol) would then yield methyl tertiary amyl ether (TAME). Alternatively a mixture of alcohols, e.g., a mixture of $C_1$-$C_5$ alcohols, could be reacted to give a mixture of alkyl tert-alkyl ethers.

The catalysts used to effect this reaction are silica-alumina clays. Chemically, clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in reaction (Eq. 2) are smectite clays. Smectite clays are discussed in the article cited in Chem. Systems Report, 84-3. These clays have small particle size and unusual intercalation properties which afford them high surface area. They are alumino silicates with a unique structure that permits modifications which should provide useful catalysts. They comprise layered sheets of octahedral sites between sheets of tetrahedral sites, where the distance between the layers can be adjusted by swelling. This layering is illustrated in an article by F. Figueras, Catal. Rev.-Sci. Eng., 30, 457 (1988). What renders the smectites of interest among the clay minerals is the combination of cation exchange, intercalation, and the fact that the distance between the layers can be adjusted by treatment with the appropriate solvent etc.

The three layered sheet types include montmorillonite, vermiculite and some brittle mica. The idealized basic structure of clays of this type is that of a pyrophyllite which has the basic formula $Si_8Al_4O_{20}(OH)_4$.

A general representation of the montmorillonite structure is:

$$M_{x/n}{}^{n+} \cdot yH_2O(Al_{4-x}Mg_x)(Si_8)O_{20}(OH)_4$$

Where:

M represents the interlamellar (balancing cations), normally sodium or lithium. x, y and n are integers.

Said montmorillonite clays are employed in the present application in neutral or slightly basic form. Clays pretreated with acid such as are described in copending U.S. patent application Ser. No. 07/494,280 do not provide the best results in the instant invention as demonstrated in Comparative Example 4 and Table VIII.

The clay component of the catalyst used in the present invention may comprise a neutral to basic clay (i.e. having a pH of about 7 or greater), have a surface area of greater than 30 m²/g, and a moisture content in the range from zero to 20 wt %.

Engelhard Corporation's Grade F2C is an acceptable commercially available montmorillonite clay. Grade F2C has a surface area of >30 m²/g, a reported moisture content of 16 wt % and a pH of 7.5.

The hydrogen fluoride-modified zeolite is prepared by treating the montmorillonite clay with hydrogen fluoride, an aqueous solution of hydrofluoric acid, or a solution of HF in a suitable organic solvent. Preferably the hydrogen fluoride is added to said zeolite as a solution of hydrofluoric acid in distilled water. Methods of preparing these HF-modified clay catalysts are illustrated in accompanying Example 1. Optionally, said formed catalysts may be calcined, typically at temperatures from 100° C. to 600° C.

The concentration of fluorine in the total catalyst may vary. The amount of fluorine can be as low as 0.1 wt % or lower of the total weight of the catalyst to obtain good results or it can be as high as 10.0 wt %. The range which seems to work well is when the fluorine comprises from 1.0 to 5.0 wt % of the total weight of the catalyst.

Said catalysts may be in the form of powders, pellets, granules, spheres, shapes and extrudates. The examples described herein demonstrate the advantages of using clay powders.

The reaction may be carried out in either a stirred slurry reactor or in a fixed bed continuous flow reactor. The catalyst concentration should be sufficient to provide the desired catalytic effect.

Etherification can generally be conducted at temperatures from 20° to 250° C.; the preferred range is 80° to 200° C. The total operating pressure may be from 0 to 1000 psig, or higher. The preferred pressure range is 50 to 500 psig.

Typically, MTBE is generated continuously in up to ca. 30+ wt % concentration in the crude liquid product at total liquid hourly space velocities (LHSV) of up to 5 or higher and relatively mild conditions, where:

$$LHSV = \frac{\text{Volume Of Total Liquid Feed Run Through The Reactor Per Hour}}{\text{Volume of Catalyst In Reactor}}$$

Crude product mixtures, comprising MTBE, isobutylene, water and unreacted methanol plus t-butanol, may, under certain circumstances, comprise two phases where the TBA conversion levels are high (i.e. >80%). These two phases would generally be composed of an isobutylene/MTBE-rich phase, and an aqueous methanol-rich phase. Such a separation is particularly advantageous in allowing the MTBE product to be easily isolated from the crude product mix, while the isobutylene by-product could be fed to a second etherification unit (with added methanol) in order to generate additional MTBE. Preferably such a product phase separation would be achieved at as low an etherification temperature as possible, but particularly in the range 160–200° C.

The examples which follow illustrate the one-step synthesis of MTBE from TBA and MeOH (Eq. 2) using the hydrogen fluoride-modified montmorillonite silica-alumina catalysts.

Conversions of t-butanol (TBA, wt %) are estimated in the following examples using the equation:

$$\frac{(\text{Wt \% Conc. of } TBA \text{ in Feed} - \text{Wt \% Conc. of } TBA \text{ in Product})}{\text{Wt \% Conc. of } TBA \text{ in Feed}} \times 100$$

Yields of methyl t-butyl ether (MTBE, mole %) are estimated from:

$$\frac{\text{Moles of } MTBE \text{ in Product Liquid}}{\text{moles of } TBA \text{ converted}} \times 100$$

Examples 1 through 4 illustrate the one-step synthesis of MTBE from TBA and MeOH using hydrogen fluoride-modified clay catalysts, particularly montmorillonite clays. The examples are only intended as a means of illustration and it is understood the invention is not meant to be limited thereby.

1) Comparing Data in Table I and Example 2 using the hydrogen fluoride-treated montmorillonite clay, prepared by the method of Example 1, with data for the untreated clay (Comparative Example A and Table VIII) it may be noted that:
   a) The TBA conversion levels with the hydrogen fluoride-treated clay of Example 2 at all operating temperatures are measurably higher than for the untreated clay.
   b) Only the hydrogen fluoride-treated clay of Example 2 achieves product phase separation into an isobutylene-MTBE product-rich phase and a heavier aqueous methanol phase at the 160°–180° C. operating temperatures.
2) Excellent etherification catalyst activity and life are achieved in Example 3 and Table IV with the same hydrogen fluoride-treated clay of Example I where the feedstock is a crude TBA/MeOH mix of defined composition. The constant performance of this catalyst over 50 days is further illustrated in accompanying FIG. I.
3) By contrast, a substantial decline in TBA conversion is evidenced over a moderate period (18 days) in Example 4 and Table VII where the catalyst is a hydrogen fluoride-loaded montmorillonite clay that has previously been treated with sulfuric acid.

EXAMPLE 1

This example illustrates the preparation of a hydrogen fluoride-modified montmorillonite clay.

To 100 g of neutral to basic montmorillonite clay (Engelhard Grade F2C, powder) was added a solution of 48% hydrofluoric acid (20 g) in distilled water (180 g). The mixture was stirred for 3–4 days at room temperature, the solids allowed to settle and the liquid decanted off. The residual solids were washed with distilled water, then methanol and dried at 150° C. in vacuo, followed by calcining at 500° C. for 2 hours.

The recovered grey/white powder was found to comprise, by analysis:

| | |
|---|---|
| Fluoride | 1.23% |
| Water | 0.42% |
| Acidity | 0.04 meq/q |

EXAMPLE 2

This example illustrates the production of methyl t-butyl ether from t-butanol and methanol using a hydrogen fluoride-modified montmorillonite clay.

Synthesis was conducted in a tubular reactor (½" i.d., 12" long), constructed of 316 stainless steel, operated upflow and mounted in a furnace controllable to ±1.0° C. and fitted with pumps allowing flow control to <±1 cc/hr. The reactor was also fitted with a pressure regulating device and equipment for monitoring temperature, pressure and flow rate.

The reactor was charged at the beginning of the experiment with 25 cc of hydrogen fluoride-treated clay powder, prepared by the method of Example 1. A screen of glass wool was placed at the top and bottom of the reactor to ensure the catalyst would remain in the middle portion.

The catalyst bed was treated with a methanol/t-butanol (1.1:1 molar mix) upflow, at a flow rate of 50 cc/hr, while the reactor was held at 120° C., with a total pressure of 300 psi. Samples of crude product effluent were collected periodically on-stream, in 316 ss bombs and analyzed by glc and gc-ir.

Typical analyses data for samples taken under these conditions are summarized in Table I. Performance at a series of other temperatures (140°, 160°, 180° C.) was determined, after lining out the unit overnight, using the same procedures. These results are also given in Tables I and II. Of note, t-butanol conversion levels at 140° and 160° C. are as follows:

TABLE I

| SAMPLE | OPERATING TEMP. (°C.) | TBA CONV. (%) |
|---|---|---|
| 4 | 140 | 52 |
| 5 | 160 | 84 |

Product phase separation into a product isobutylene-MTBE rich phase and a heavier aqueous methanol phase was achieved at both the 160° C. and 180° C. operating temperatures.

TABLE II

MTBE From MEOH/TBA

| Ex. | Catalyst | MeOH/TBA Molar Ratio | Temp. (°C.) | Feed Rate (cc/hr) | Time On Stream (Days) | SAMPLE | H₂O | MeOH | C₄H₈ | TBA | MTBE |
|---|---|---|---|---|---|---|---|---|---|---|---|
| 2 | Ex. 1 | 1.1:1 | | | | FS-1 | | 32.5 | | 67.1 | |
| | | | 120 | 50 | 1 | 1 | 3.4 | 28.4 | 4.1 | 51.1 | 12.7 |
| | | | | | | 2 | 3.8 | 30.1 | 4.1 | 49.4 | 12.3 |
| | | | 140 | | 2 | 3 | 7.7 | 23.8 | 9.2 | 32.4 | 26.7 |
| | | | | | | →4 | 8.0 | 24.1 | 9.0 | 32.2 | 26.5 |
| | | | 160 | | 3 | →5 { | 9.9 | 22.1 | 25.8 | 11.0 | 30.9 |
| | | | | | | | 30.2 | 37.5 | 6.6 | 10.5 | 14.9 |
| | | | | | | 6 { | 9.0 | 21.2 | 27.4 | 10.8 | 31.4 |
| | | | | | | | 30.7 | 38.1 | 6.3 | 10.1 | 14.5 |
| | | | 180 | | 4 | 7 { | 0.8 | 7.8 | 68.9 | 2.8 | 19.4 |
| | | | | | | | 29.6 | 52.2 | 5.8 | 5.6 | 6.4 |
| | | | | | | 8 { | 0.9 | 8.1 | 68.6 | 2.8 | 19.5 |
| | | | | | | | 29.7 | 52.3 | 5.7 | 5.6 | 6.3 |

EXAMPLE 3

This example illustrates the performance of a hydrogen fluoride-modified clay in the production of methyl t-butyl ether from a crude t-butanol/methanol feedstock over an extended period.

Using the equipment and procedures of Example 2, 25 cc of the HF-modified clay of Example 1 was charged to the reactor system and performance was monitored at 140° C. using a crude feed mix comprising t-butanol, methanol, water, MTBE, acetone ($Ac_2O$), iso-propanol (2-PrOH), di-t-butyl peroxide (DTBP) and t-butyl formate (TBF). The TBA/MeOH molar feed ratio was 1:2. The feed rate was maintained at 50 cc/hr. The results are summarized in Tables III and IV.

TABLE III

| SAMPLE | TIME ON STREAM (DAYS) | TBA CONV. (%) | MOLAR SELECTIVITIES (%) | |
|---|---|---|---|---|
| | | | C₄H₈ | MTBE |
| 2 | 9 | 71 | 24 | 71 |
| 8 | 42 | 71 | 31 | 65 |

Typical concentrations of MTBE, isobutylene and t-butanol in the crude product effluents from the run are also plotted in FIG. 1.

TABLE IV

MTBE From MEOH/TBA

| Ex. | Catalyst | MeOH/TBA Molar Ratio | Temp. (°C.) | Feed Rate (cc/hr) | Time On Stream (Days) | SAMPLE | H₂O | MeOH | C₄H₈ | Ac₂O | 2PrOH | TBA | MTBE | DTBP | TBF |
|---|---|---|---|---|---|---|---|---|---|---|---|---|---|---|---|
| 3 | Ex. 1 | 2:1 | 140 | 50 | | FS-1 | 5.8 | 41.2 | | 0.5 | 1.2 | 49.2 | 2.1 | 3.7 | 0.14 |
| | | | | | 1 | 1 | 11.1 | 34.8 | 4.1 | 1.1 | 1.1 | 29.3 | 18.2 | 1.9 | 0.01 |
| | | | | | 9 | →2 | 14.7 | 30.9 | 6.3 | 1.0 | 1.1 | 14.2 | 31.6 | 2.4 | 0.02 |
| | | | | | 15 | 3 | 14.5 | 30.6 | 6.2 | 1.2 | 1.3 | 14.0 | 31.8 | 2.6 | 0.01 |
| | | | | | 18 | 4 | 14.5 | 30.6 | 6.5 | 1.2 | 1.3 | 13.8 | 31.9 | 2.6 | 0.01 |
| | | | | | 22 | 5 | 14.4 | 30.6 | 7.4 | 1.2 | 1.3 | 13.5 | 31.2 | 2.5 | 0.01 |
| | | | | | 31 | 6 | 14.4 | 30.2 | 6.5 | 1.4 | 1.4 | 15.3 | 30.3 | 3.0 | 0.01 |
| | | | | | | FS-2 | 5.3 | 41.0 | | 0.5 | 1.5 | 49.7 | 2.0 | 4.6 | 0.17 |
| | | | | | 37 | 7 | 14.6 | 30.1 | 6.5 | 1.3 | 1.4 | 15.5 | 30.3 | 2.9 | 0.01 |
| | | | | | 42 | →8 | 14.7 | 30.4 | 8.3 | 1.3 | 1.4 | 14.2 | 29.3 | 3.1 | 0.01 |
| | | | | | 48 | 9 | 11.7 | 31.0 | 12.4 | 1.2 | 1.4 | 8.5 | 33.5 | 4.3 | 0.01 |
| | | | | | 50 | 10 | •15.3 | 30.1 | 6.0 | 1.2 | 1.5 | 16.0 | 29.7 | 3.2 | 0.01 |

EXAMPLE 4

This example illustrates the performance of another hydrogen fluoride-modified clay in the production of methyl t-butyl ether from a crude t-butanol/methanol feedstock.

Using the procedures of Examples 2 and 3, 50 cc of a sample of 4.5 % HF-loaded montmorillonite clay that had been previously acidified with sulfuric acid was charged to the reactor system and performance was monitored at 140° C. using a crude feed mix comprising t-butanol, methanol, water, MTBE, acetone, isopropanol, di-t-butyl peroxide and t-butyl formate. The TBA/MeOH molar feed ratio was 1:2. The feed rate was maintained at ca. 100 cc/hr. The results are summarized in Tables V and VI.

Calculated TBA conversion and $C_4H_8$/MTBE selectivities for typical samples are as follows:

TABLE V

| SAMPLE | TIME ON STREAM (DAYS) | TBA CONV. (%) | MOLAR SELECTIVITIES (%) | |
|---|---|---|---|---|
| | | | $C_4H_8$ | MTBE |
| 1 | 1 | 53 | 18 | 83 |
| 7 | 18 | 19 | 22 | 80 |

COMPARATIVE EXAMPLE A

This comparative example illustrates the performance of an unmodified montmorillonite clay in the production of methyl t-butyl ether from t-butanol and methanol over a range of conditions.

Using the equipment and procedures of Examples 2, 25 cc of neutral montmorillonite clay (Engelhard F2C powder) was charged to the reactor system and temperature was monitored over a range of operating temperatures (120°-180° C.). The results are summarized in Tables VII and VIII.

Calculated TBA conversions at 140° C. and 160° C. are typically as follows:

TABLE VII

| SAMPLE | OPERATING TEMP. (°C.) | TBA CONV. (%) |
|---|---|---|
| 3 | 140 | 6 |
| 6 | 160 | 25 |

No product phase separation was in evidence during this experiment.

TABLE VI

MTBE From MEOH/TBA

| Ex. | MeOH/TBA Molar Ratio | Temp. (°C.) | Feed Rate (cc/hr) | Time On Stream (Days) | SAMPLE | H₂O | MeOH | C₄H₈ | AC₂O | 2PrOH | TBA | MTBE | DTBP | TBF |
|---|---|---|---|---|---|---|---|---|---|---|---|---|---|---|
| 4 | 2:1 | 140 | 100 | | FS | 5.6 | 40.8 | | 0.6 | 1.4 | 49.3 | 2.1 | 4.8 | 0.18 |
| | | | | 1 | →1 | 12.4 | 30.9 | 3.6 | 0.6 | 1.4 | 23.2 | 27.9 | 5.1 | — |
| | | | | 3 | 2 | 11.0 | 32.8 | 3.4 | 0.5 | 1.4 | 28.8 | 21.9 | 4.7 | 0.01 |
| | | | | 4 | 3 | 10.7 | 33.2 | 3.2 | 0.5 | 1.4 | 30.1 | 20.8 | 4.8 | 0.01 |
| | | | | 7 | 4 | 9.4 | 35.4 | 2.6 | 0.5 | 1.4 | 34.7 | 16.0 | 4.6 | 0.01 |
| | | | | 9 | 5 | 9.1 | 35.5 | 2.5 | 0.5 | 1.4 | 35.5 | 15.3 | 4.7 | 0.01 |
| | | | | 14 | 6 | 8.8 | 36.1 | 2.3 | 0.5 | 1.4 | 36.9 | 13.9 | 4.7 | 0.01 |
| | | | | 18 | →7 | 8.0 | 37.2 | 1.9 | 0.5 | 1.3 | 39.7 | 11.3 | 4.7 | — |

TABLE VIII

MTBE From MEOH/TBA

| Ex. | Catalyst | MeOH/TBA Molar Ratio | Temp. (°C.) | Feed Rate (cc/hr) | Time On Stream (Days) | SAMPLE | H₂O | MeOH | C₄H₈ | TBA | MTBE |
|---|---|---|---|---|---|---|---|---|---|---|---|
| | Clay-2C | | | | | FS-1 | | 31.4 | | 67.9 | |
| | | | 120 | 50 | 1 | 1 | 0.1 | 31.4 | 0.2 | 67.7 | 0.4 |
| | | | | | | 2 | 0.2 | 31.3 | 0.3 | 67.4 | 0.6 |
| | | | 140 | 50 | 2 | →3 | 1.3 | 30.7 | 1.0 | 63.9 | 2.9 |

TABLE VIII-continued

| Ex. | Catalyst | MeOH/TBA Molar Ratio | Temp. (°C.) | Feed Rate (cc/hr) | Time On Stream (Days) | MTBE From MEOH/TBA PRODUCT COMPOSITION (WT %) | | | | | |
|---|---|---|---|---|---|---|---|---|---|---|---|
| | | | | | | SAMPLE | H$_2$O | MeOH | C$_4$H$_8$ | TBA | MTBE |
| | | | | | | 4 | 0.8 | 30.8 | 0.9 | 64.7 | 2.5 |
| | | | 160 | 50 | 3 | 5 | 3.0 | 28.2 | 3.5 | 55.5 | 9.5 |
| | | | | | | →6 | 4.4 | 27.3 | 4.5 | 50.6 | 12.9 |
| | | | 180 | 50 | 4 | 7 | 10.0 | 22.1 | 12.8 | 26.5 | 28.2 |
| | | | | | | 8 | 9.9 | 22.4 | 12.6 | 26.9 | 27.9 |

What is claimed is:

1. In a method wherein a C$_4$–C$_{10}$ tertiary alcohol is reacted with a C$_1$–C$_6$ primary alcohol in a reaction zone in the presence of a catalyst to provide alkyl-tert-alkyl ethers the improvement of accomplishing the reaction in one-step which comprises using as a catalyst a hydrogen fluoride-modified montmorillonite clay and continuously contacting said tertiary alcohol and primary alcohol in the molar ratio of primary alcohol to tertiary alcohol in the range of 1 to 5 with said catalyst at a temperature of about 20° C. to 250° C. and a pressure of about atmospheric to about 1000 psig to obtain the alkyl-tert-alkyl ether product.

2. The method of claim 1 wherein the C$_4$–C$_{10}$ tertiary alcohol is selected from the group consisting of tertiary butanol and tertiary amyl alcohol.

3. The method of claim 1 wherein the C$_1$–C$_6$ primary alcohol is selected from the group consisting of methanol, ethanol, n-propanol and n-hexanol.

4. The method of claim 1 wherein the tertiary alcohol is t-butanol and the primary alcohol is methanol.

5. The method of claim 1 wherein the hydrogen fluoride is an aqueous solution of hydrofluoric acid.

6. The method of claim 1 wherein the clay has the structure:

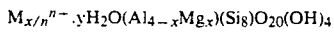

$$M_{x/n}^{n-} \cdot yH_2O(Al_{4-x}Mg_x)(Si_8)O_{20}(OH)_4$$

where: M represents the interlamellar balancing cations, normally sodium or lithium and x, y and n are integers.

7. The method of claim 1 wherein the wt % of fluoride in the total weight of the catalyst is 0.1% to 10.0 wt %.

8. The method of claim 1 wherein said montmorillonite clay has a surface area of at least 30 m$^2$/gm.

9. The method of claim 1 wherein said montmorillonite clay has a moisture content of up to 20 wt %.

10. The method of claim 1 wherein said hydrogen fluoride-modified montmorillonite clay is in powder or granular form.

11. A method for the co-production of methyl tertiary butyl ether plus isobutylene wherein tertiary butanol is reacted with methanol in a reaction zone in the presence of a hydrogen fluoride-modified montmorillonite clay catalyst having a concentration of fluoride of 0.1 to 10.0 wt % of the total weight of the catalyst, a surface area of >30 m$^2$/gm and a moisture content up to 20 wt % at a temperature of 80° to 200° C. and a pressure of about atmospheric to about 1000 psi.

12. The method of claim 11 wherein the methanol to t-butanol feed molar ratio is in the range 1:10 to 10:1.

13. The method of claim 11 wherein the t-butanol conversion level is >80% and the crude product mix comprising methyl tertiary butyl ether, isobutylene, unreacted methanol plus t-butanol and water is two phases.

14. The method of claim 13 wherein the two-phase product mix comprises an isobutylene plus MTBE-rich phase, and an aqueous methanol-rich phase.

* * * * *